(12) United States Patent
Imamura et al.

(10) Patent No.: US 7,189,572 B2
(45) Date of Patent: Mar. 13, 2007

(54) METHOD FOR MEASURING WATER CONTENT OF FUEL CELL BASED ON CONDUCTIVITY OF ELECTROLYTE

(75) Inventors: Tomonori Imamura, Kariya (JP); Toshiyuki Kawai, Okazaki (JP); Kunio Okamoto, Okazaki (JP)

(73) Assignee: Denso Corporation, Kariya (JP)

( * ) Notice: Subject to any disclaimer, the term of this patent is extended or adjusted under 35 U.S.C. 154(b) by 668 days.

(21) Appl. No.: 10/151,195

(22) Filed: May 20, 2002

(65) Prior Publication Data

US 2002/0180448 A1    Dec. 5, 2002

(30) Foreign Application Priority Data

May 18, 2001  (JP)  ............................. 2001-149936
Apr. 3, 2002   (JP)  ............................. 2002-101419

(51) Int. Cl.
*G01N 31/00* (2006.01)

(52) U.S. Cl. .................. 436/39; 436/149; 436/150; 422/68.1; 422/82.01

(58) Field of Classification Search .................. 436/39, 436/149, 150; 422/68.1, 82.01, 82.02
See application file for complete search history.

(56) References Cited

U.S. PATENT DOCUMENTS 6,524,733 B1 *  2/2003  Nonobe ........................ 429/23

6,790,549 B2     9/2004  Nonobe

FOREIGN PATENT DOCUMENTS

| JP | A-7-288136 | 10/1995 |
| JP | 11-191423  | 7/1999  |

OTHER PUBLICATIONS

Examination Report of corresponding JP Application No. 2002-101419 dated Aug. 23, 2006.

* cited by examiner

*Primary Examiner*—Jill Warden
*Assistant Examiner*—Sam P. Siefke

(57) ABSTRACT

A measuring method first calculates the conductivity of an electrolyte membrane based on measured output voltage and output current of a fuel cell. The water content of an oxidant channel as an index of present water content (PWC) of the fuel cell is calculated based on the calculated conductivity and the other measured physical quantities of the fuel cell. Further the method calculates the water content of the oxidant channel after the inside of the fuel cell reaches a steady state as an index of future water content (FWC) using the measured physical quantities. The PWC index and FWC index are compared, and it is finally determined, based on the result of the comparison and the difference between the previous and present values of the conductivity, whether the water content of the fuel cell is short or excessive at the present time.

10 Claims, 8 Drawing Sheets

METHOD FOR MEASURING WATER CONTENT OF FUEL CELL BASED ON CONDUCTIVITY OF ELECTROLYTE

CROSS REFERENCE TO RELATED APPLICATION

The present application is based on and incorporates herein by reference Japanese Patent Applications No. 2001-149936 filed on May 18, 2001 and No. 2002-101419 filed on Apr. 3, 2002.

BACKGROUND OF THE INVENTION

1. Field of the Invention

The present invention relates to a fuel cell suitable for a vehicle, a boat, a portable generator or a small generator for household use and, more particularly, to a method for measuring water content of the fuel cell.

2. Related Art

In a fuel cell with a short water content, the electrolyte membrane has high resistance because it is dry. Therefore the fuel cell outputs a lower voltage in comparison with a fuel cell with the proper water content, even when the same amount of current is outputted. On the other hand, in a fuel cell with an excessive water content, the water in the fuel cell prevents the gas from diffusing toward the reaction site. Therefore the fuel cell with an excessive water content also outputs a lower voltage in comparison with a fuel cell with the proper water content.

Accordingly, the water content of the fuel cell should be adjusted to a proper value in order that the fuel cell operates efficiently. However, no method for measuring the water content of the fuel cell is known, and therefore shortage or excess of the water content cannot be detected. Accordingly the water content of the fuel cell cannot be appropriately adjusted.

SUMMARY OF THE INVENTION

The present invention has an object to provide a method for estimating the water content of a fuel cell based on physical quantities of the fuel cell.

A method according to the present invention measures the water content of the inside of a fuel cell. The method first obtains the conductivity of the solid electrolyte of the fuel cell, and estimates, as an index of present water content (PWC), water content of the inside of the fuel cell based on the obtained conductivity of the electrolyte. Further the method estimates, as an index of future water content (FWC), water content of the inside of the fuel cell at a time point when time elapsed after said PWC index is measured reaches a predetermined length. Then the PWC index and the FWC index are compared, and it is determined whether the water content of the inside of the fuel cell is short or excessive based on the result of the comparison.

Preferably, the output voltage and the output current of the fuel cell is measured, and a voltage drop corresponding to the resistance of the electrolyte is estimated based on the measured output voltage. Then the resistance of the electrolyte is calculated by dividing the voltage drop by the measured output current. Further the reciprocal of the resistance is calculated. Then the conductivity of the electrolyte, which is used for estimating the PWC index, is calculated using the reciprocal of the resistance.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENT (First Embodiment)

Figure 1:
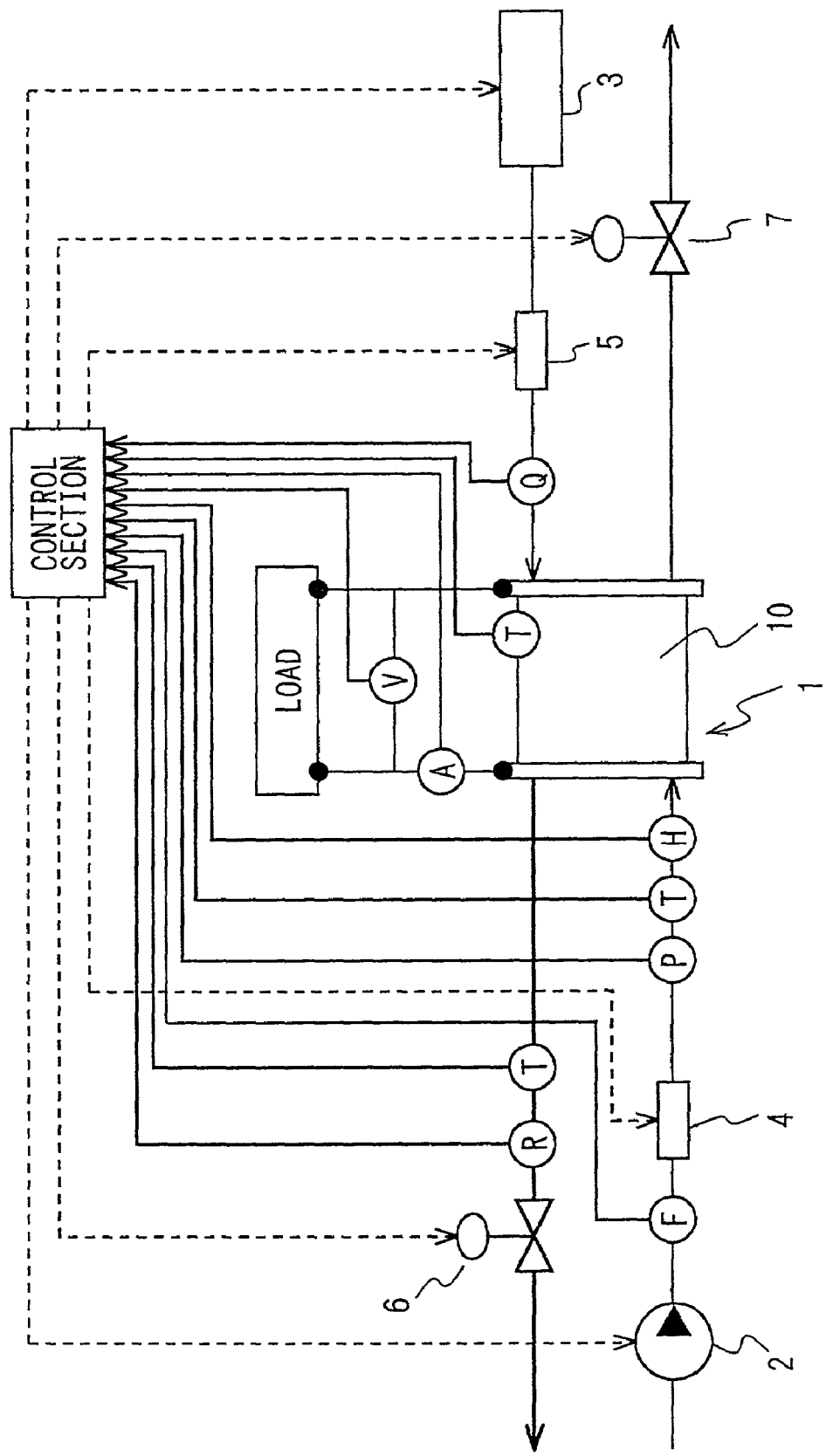
FIG. 1 is a schematic diagram showing a system for measuring water content of a fuel cell according to a first embodiment of the present invention.

Referring to FIG. 1, a system for measuring the water content of a fuel cell 1 according to a first embodiment of the present invention includes the fuel cell 1, a control section, a load, a compressor 2, hydrogen supply equipment 3, first and second humidifiers 4, 5, first and second back-pressure control valves 6, 7 and various sensors A, F, H, P, Q, R, T, V. The fuel cell 1 includes a solid electrolyte membrane 10, and a catalyst layer and a diffusion layer are formed on either side of the electrolyte membrane 10. Further a fuel channel and an oxidant channel are formed on the respective sides of the electrolyte membrane 10. The compressor 2 supplies air to the fuel cell 1. The hydrogen supply equipment 3 supplies hydrogen to the fuel cell 1. The first control valve 6 is disposed on the exhaust air passage, while the second control valve 7 is disposed on the exhaust hydrogen passage.

A current sensor A is serially connected between the fuel cell 1 and the load. A mass flow sensor F is disposed on the outlet side of the compressor 2. A humidity sensor H is disposed on the inlet air passage. Pressure sensors P, Q, R are disposed on the inlet air passage, the inlet hydrogen passage and the exhaust air passage, respectively. Temperature sensors T are disposed in the fuel cell 1, on the inlet air passage and the exhaust air passage, respectively. A voltage sensor V is connected in parallel between the fuel cell 1 and the load.

The control section is a microcomputer, and receives sensor signals from the sensors A, F, H, P, Q, R, T, V. Then control section controls the compressor 2, the hydrogen supply equipment 3, the humidifiers 4, 5, and control valves 6, 7.

Figure 2:
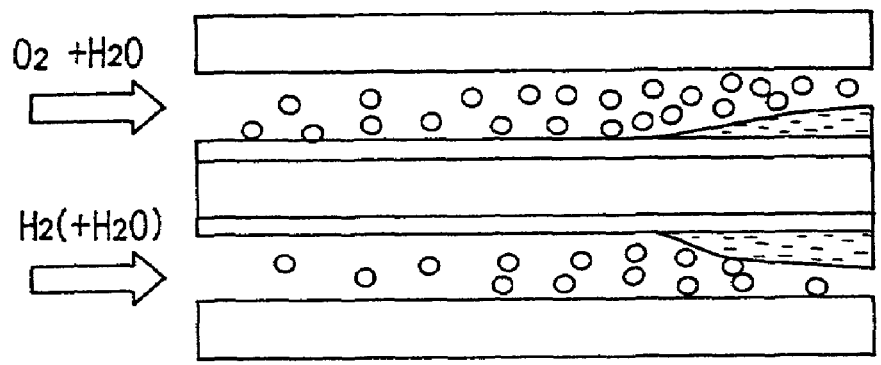
FIG. 2 is a schematic diagram showing how water generated during operation of the fuel cell accumulates in the channels of the fuel cell.

Electric power is produced as a part of an electrochemical reaction between hydrogen and oxygen. Therefore water is generated when the electric power is produced, and the amount of generated water depends on the amount of generated currents. The generated water moves towards the outlet of the oxidant channel, and accumulates and condenses on the downstream side of the oxidant channel as shown in FIG. 2. Some of the condensed water is drained from the oxidant channel. However, the rest of the condensed water is left in the oxidant channel, and distributes over the oxidant channel.

The water content at a point on electrolyte membrane 10 decreases as the water content at the corresponding point in the oxidant channel decreases. The conductivity at a point on the electrolyte membrane 10 decreases as the water content at the point decreases. Therefore, as the water distribution in the oxidant channel varies, the distribution of conductivity of the electrolyte membrane 10 varies and therefore the average conductivity of the electrolyte membrane 10 varies. As a result, the output voltage of the fuel cell 1 varies. That is, the output voltage of the fuel cell 1 usually lowers as the water content of the oxidant channel decreases. However, when the water content of the oxidant channel is excessive, the output voltage of the fuel cell 1 lowers as the water content of the oxidant channel further increases, because the water in the oxidant channel prevents the gas from diffusing toward the reaction site.

That is, the water content of the fuel cell 1 can be estimated based on the output voltage of the fuel cell 1 because the output voltage varies depending on the water content of the fuel cell 1. However a drop in the output voltage due to shortage of water content of the electrolyte membrane 10 should be discriminated from a drop in the output voltage due to excess of water content of the oxidant channel. Accordingly the control section estimates the water content of the fuel cell 1 as follows.

Figure 3:
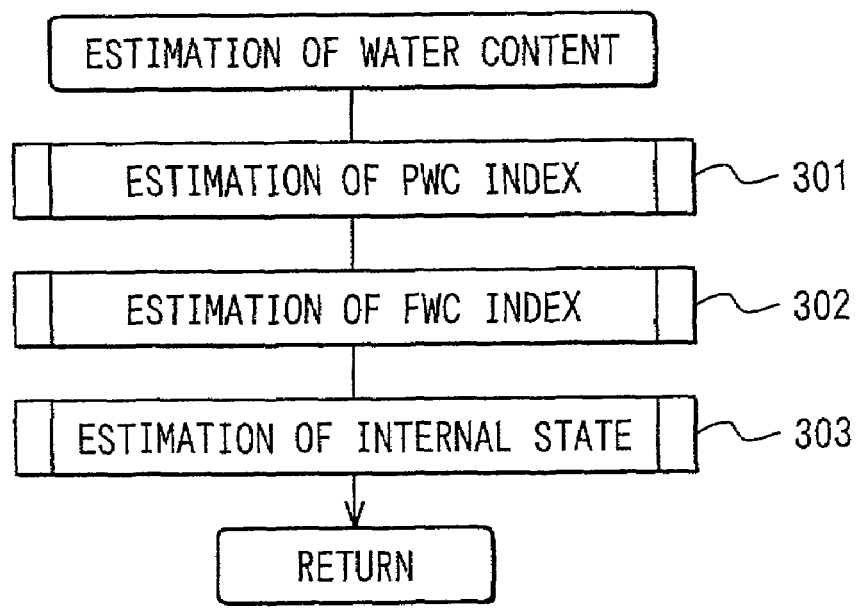
FIG. 3 is a flowchart of a routine which causes the control section of the system shown in FIG. 1 to estimate the water content of the fuel cell according to the first embodiment upon execution by the control section.

Referring to FIG. 3, at step 301, the output voltage and the output current of the fuel cell 1 are measured, and a voltage drop corresponding to the resistance of the electrolyte membrane 10 is derived from the measured output voltage and current. The resistance of the electrolyte membrane 10 is calculated by dividing the voltage drop by the measured output current, and the reciprocal of the resistance is further calculated as the conductivity (i.e., the average conductivity) of the electrolyte membrane 10. Then the conductivity distribution is derived from the average conductivity by back calculation. The water distribution is estimated based on the conductivity distribution. Then the water content of the fuel cell 1 as an index of present water content (PWC) is obtained from the water distribution.

At step 302, the water content at a time point after an interval is estimated as an index of future water content (FWC) assuming that the operating condition (flow rate, temperature and pressure of or in the gas) of the fuel cell 1 at the time of measurement of the voltage and the current is maintained for the interval. The interval corresponds to time taken to reach a steady state if the operation condition is maintained. At step 303, the PWC index and the FWC index are compared, and the previous conductivity and the present conductivity of the electrolyte membrane 10 are compared. Then it is determined whether the water content of the fuel cell 1 is excessive or short at the present time based on the result of the comparison.

Figure 4:
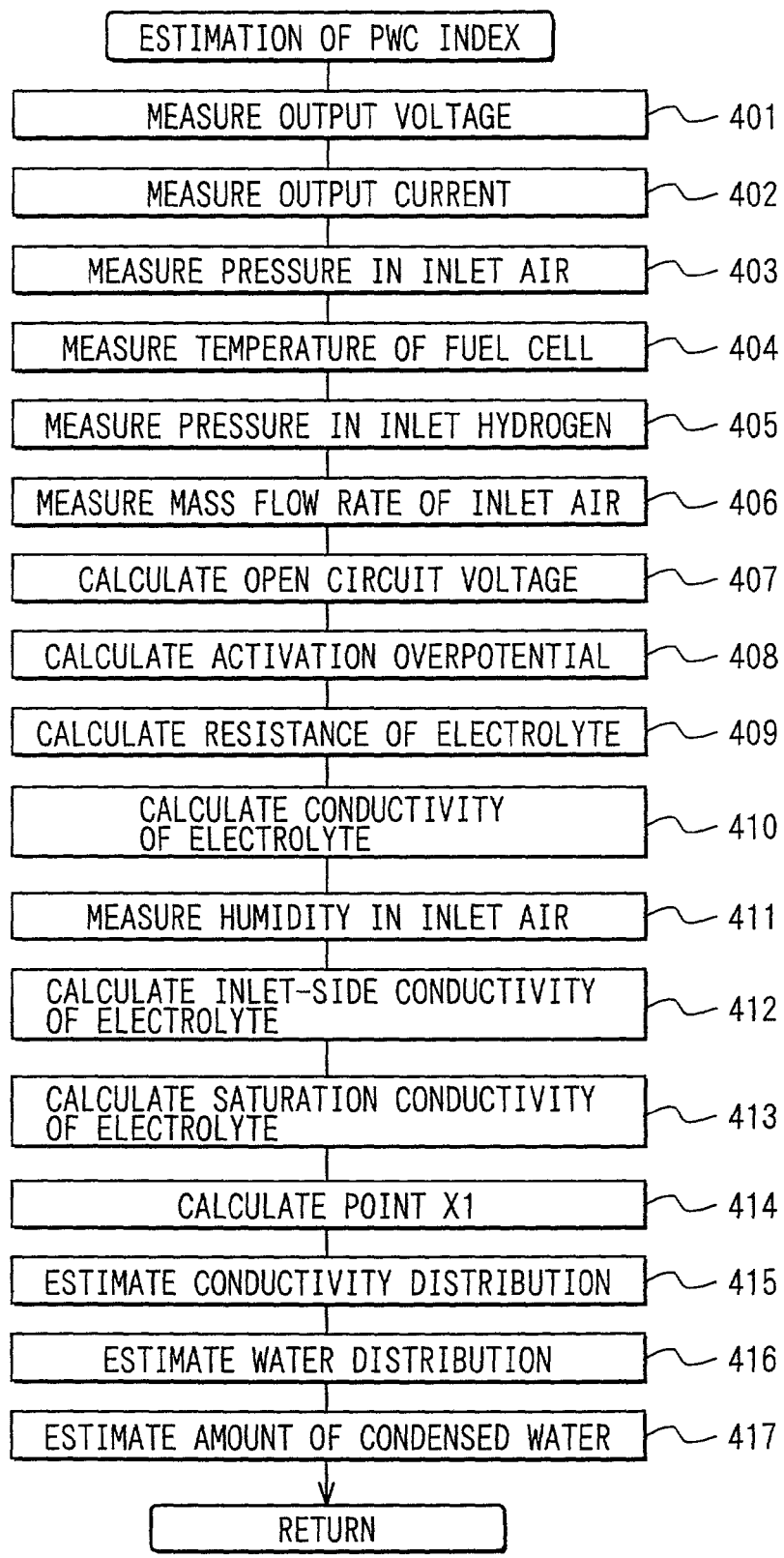
FIG. 4 is a flowchart of a subroutine which causes the control section to estimate an index of present water content (PWC) in the fuel cell upon execution at step 301 of FIG. 3.

More specifically, the PWC index is estimated at step 301 as follows. Referring to FIG. 4, the output voltage $V_1$ and output current I of the fuel cell 1 are measured by the voltage sensor V and the current sensor A at steps 401 and 402, respectively. Then the physical quantities that determine an open circuit voltage of the fuel cell 1 are measured at steps 403–406. The physical quantities measured at step 403–406 are the pressure in the inlet air measured by the pressure sensor P, the temperature of the fuel cell 1 measured by the temperature sensor T, the pressure in the inlet hydrogen measured by the temperature sensor Q, and the mass flow rate of the inlet air measured by the mass flow sensor F, respectively. At step 407, the open circuit voltage is calculated using the measured physical quantities. Further the activation overpotential is calculated at step 408.

Figure 5:
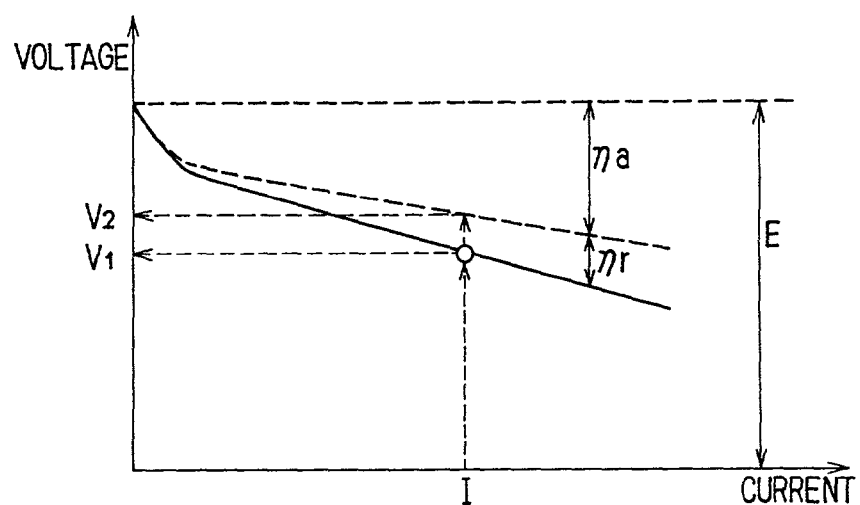
FIG. 5 is a graph showing how the output voltage and current of the fuel cell are related with an open circuit voltage, an activation overpotential and a resistance loss voltage.

The measured output voltage $V_1$ and current I are related with the open circuit voltage E, the activation overpotential $\eta_a$ and the resistance loss voltage $\eta_r$ of the fuel cell 1 as shown in FIG. 5. The activation overpotential $\eta_a$ corresponds to a voltage drop due to chemical reaction of water in the diffusion layer, while the resistance loss voltage $\eta_r$ corresponds to a voltage drop due to the resistance of the electrolyte membrane 10. Therefore the resistance Rm of the electrolyte membrane 10 is expressed as:

$$Rm=(V_2-V_1)/I \tag{1}$$

where $V_2=E-\eta_a(I)$.

Therefore the conductivity (i.e., average conductivity) of the electrolyte membrane 10 is expressed as:

$$\sigma_{mesured}=tI/S(V_2-V_1)=t\cdot R(Rm)/S \tag{2}$$

where R(Rm) is the reciprocal of the resistance Rm of the electrolyte membrane 10, t(m) is the thickness of the electrolyte membrane 10 and S(m$^2$) is the area of the electrode. The control section stores a map which represents I–$V_2$ characteristics shown in FIG. 5 beforehand. Therefore the resistance Rm of the electrolyte membrane 10 can be obtained using formula (1) based on the value of $V_2$ provided by the stored map.

Accordingly, the resistance of the electrolyte membrane 10 is calculated at step 409 using the measured output voltage $V_1$ and current I and the value of $V_2$. At step 410, the reciprocal R(Rm) of the resistance Rm is calculated and further the conductivity $\sigma_{measured}$ of the electrolyte membrane 10 is calculated using formula (2) based on the calculated reciprocal R(Rm).

Figure 6:
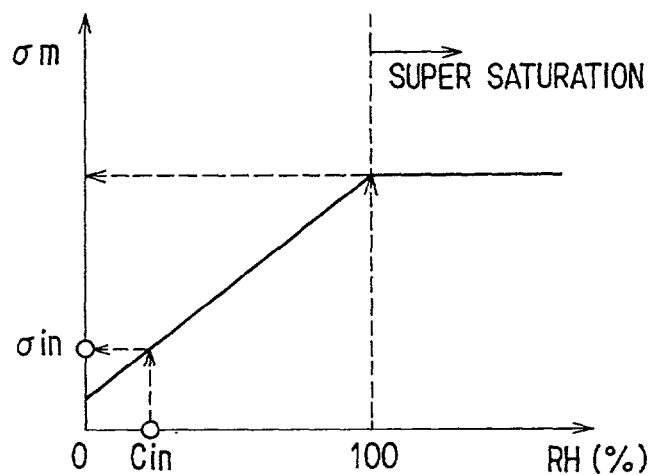
FIG. 6 is a graph showing humidity-conductivity characteristics of the electrolyte of the fuel cell.

Next, the humidity (i.e., water vapor concentration) $C_{in}$ (mol/m$^3$) in the inlet air is detected by the humidity sensor H at step 411. The humidity C in the air around the electrolyte membrane 10 generally relates with the conductivity $\sigma_m$ of the electrolyte membrane 10 as shown in FIG. 6. That is, the conductivity $\sigma_m$ of the electrolyte membrane 10 is a linear function of the humidity C. Therefore the conductivity $\sigma_{in}$ on the inlet side is expressed as:

$$\sigma_{in} = K_1(C_{in}/C_s) + K_2 \quad (3)$$

where $K_1$, $K_2$ are constants and $C_s$ is the saturated vapor concentration (mol/m$^3$). Accordingly, the inlet-side conductivity $\sigma_{in}$ of the electrolyte membrane 10 is estimated at step 412 using formula (3).

Figure 7:
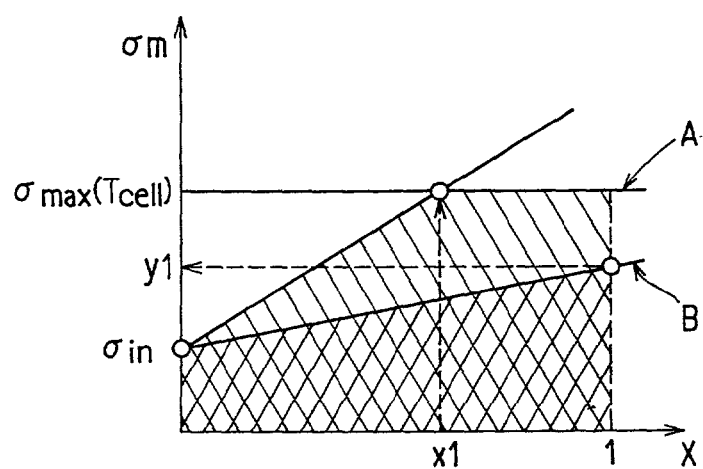
FIG. 7 is a graph showing how the conductivity of the electrolyte distributes over the oxidant channel of the fuel cell.

Generally, the conductivity $\sigma_m$ of the electrolyte membrane 10 distributes over the oxidant channel as shown in FIG. 7, because water generated in the oxidant channel accumulates on the downstream side as described above. The horizontal axis X in FIG. 7 is the scale of the point on the oxidant channel. Point 0 on the horizontal axis X corresponds to the inlet of the oxidant channel, while point 1 on the horizontal axis X corresponds to the outlet of the oxidant channel. The conductivity $\sigma_m$ at a point on the electrolyte membrane 10 increases linearly as the point comes close to the outlet, and reaches the saturation conductivity $\sigma_{max}$, which is a function of the temperature $T_{cell}$ of the fuel cell 1, at point x1 as shown by line A in FIG. 7. The conductivity $\sigma_m$ between point x1 and point 1 is constant and equals the saturation conductivity $\sigma_{max}$. That is, the electrolyte membrane 10 is saturated with water between point x1 and point 1.

Alternatively, the conductivity $\sigma_m$ at a point on the electrolyte membrane 10 increases linearly as the point comes close to the outlet, and reaches the conductivity y1 less than the saturation conductivity $\sigma_{max}$ at point 1 as shown by line B in FIG. 7. The area of a polygon defined by line A or B and the horizontal and vertical axes corresponds to the average conductivity (i.e., measured conductivity) $\sigma_{mesured}$.

Therefore, in the case that the conductivity $\sigma_m$ distributes as shown by line A, the measured conductivity $\sigma_{mesured}$ is expressed as:

$$\sigma_{mesured} = \sigma_{max} - \frac{(\sigma_{max} - \sigma_{in})}{2} x1 \quad (4)$$

Therefore point x1 at which the conductivity $\sigma_m$ reaches the saturation conductivity $\sigma_{max}$ is expressed as:

$$x1 = 2\left(\frac{\sigma_{max} - \sigma_{mesured}}{\sigma_{max} - \sigma_{in}}\right) \quad (5)$$

Accordingly the saturation conductivity $\sigma_{max}$ is calculated at step 413 based on the temperature $T_{cell}$ detected by the temperature sensor T, and point x1 at which the conductivity $\sigma_m$ reaches the saturation conductivity $\sigma_{max}$ is calculated using formula (5) at step 414.

If point x1 is equal to or larger than 0 and equal to or less than 1, the distribution of the conductivity $\sigma_m$ is represented by a line similar to line A of FIG. 7. If point x1 is larger than 1, the distribution of the conductivity $\sigma_m$ is represented by a line similar to line B of FIG. 7.

In the latter case, the maximum conductivity y1 corresponding to the point 1 is expressed as:

$$y1 = 2\sigma_{mesured} - \sigma_m \quad (6)$$

because the measured conductivity $\sigma_{mesured}$ is expressed as:

$$\sigma_{mesured} = \frac{y1 + \sigma_{in}}{2} \quad (7)$$

Therefore the conductivity y1 corresponding to point 1 is calculated formula (6). Thus the distribution of the conductivity $\sigma_m$ of the electrolyte membrane 10 is calculated at step 415.

Figure 8:
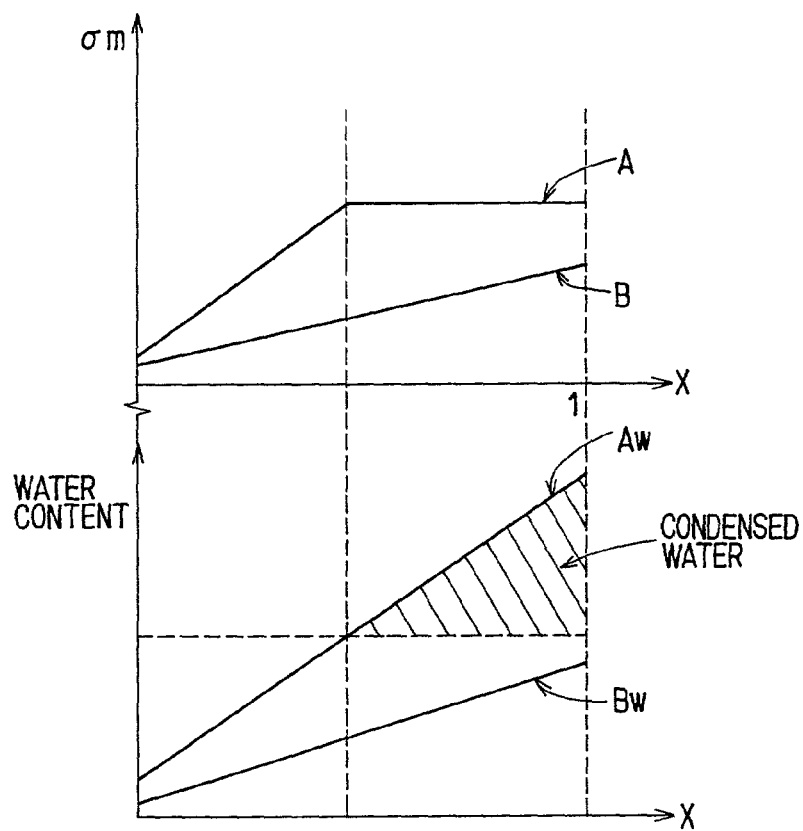
FIG. 8 is a graph showing how conductivity distribution in the electrolyte is related with water distribution in the oxidant channel.

Next the water distribution in the oxidant channel is calculated. When the conductivity $\sigma_m$ at a point on the electrolyte membrane 10 increases linearly as the point comes close to the outlet (i.e., point 1) as shown by line B in FIG. 8, it is estimated using the relation shown in FIG. 6 that the water content at a point in the oxidant channel also increases linearly as the point comes close to the outlet as shown by line Bw in FIG. 8. When the conductivity $\sigma_m$ reaches the saturation conductivity $\sigma_{max}$ in the middle of the oxidant channel as shown by line A in FIG. 8, it is estimated that the water content increases linearly as the conductivity $\sigma_m$ increases linearly. Further it is estimated that the water at a point in the oxidant channel increases linearly as the point further comes close to the outlet as shown by line Aw in FIG. 8 although the conductivity $\sigma_m$ is constant. That is, an excess of vapor over the saturation vapor concentration condenses into water at a point where the electrolyte membrane 10 is saturated with water.

In this way, the water distribution in the oxidant channel is estimated at step 416. Finally, the amount of the condensed water is estimated as the PWC index at step 417 utilizing the fact that the shaded area in FIG. 8 corresponds to the amount of the condensed water.

Figure 9:
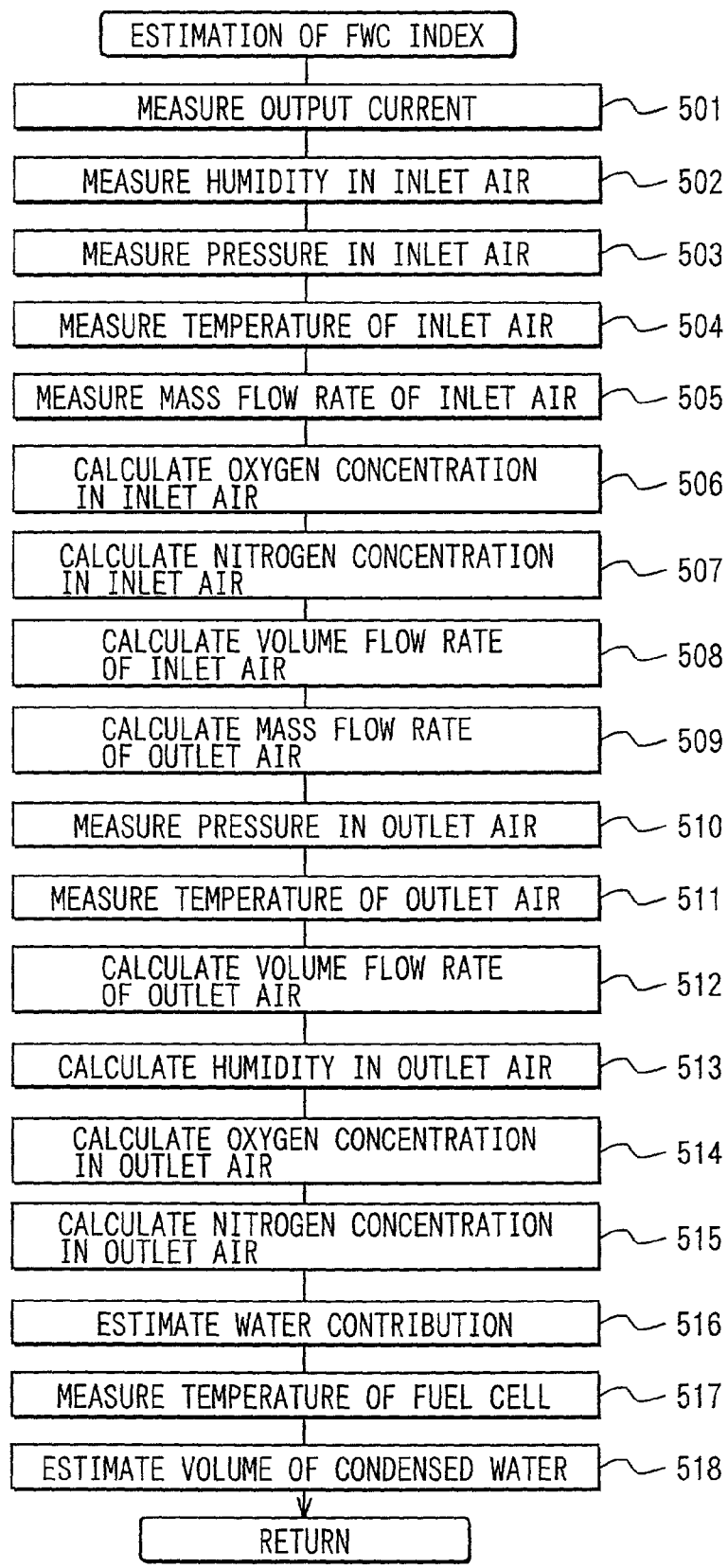
FIG. 9 is a flowchart of a subroutine which causes the control section to estimate an index of future water content (FWC) of the fuel cell upon execution at step 302 of FIG. 3.

Next the FWC index is estimated at step 302 as follows. Referring to FIG. 9, the output current of the fuel cell 1 is measured by the current sensor A at step 501. The humidity $C_{in}$ in the inlet air is measured by the humidity sensor H at step 502. Alternatively the humidity $C_{in}$ (mol/m$^3$) in the inlet air may be estimated using the following formula:

$$C_{in} = W/V_{in}(P_{in}, W, T_{in}) \quad (8)$$

where W (mol/sec) is the mass rate of humidification water, $V_{in}$ (m$^3$/sec) is the volume flow rate of humidified inlet air, $P_{in}$ (Pa) is the pressure in the inlet air and $T_{in}$ (K) is the temperature of the inlet air. The mass rate W of the humidification water may be set to the mass rate of water actually injected by an injector. Alternatively, it may be set to a value calculated based on the values measured by the humidity sensor or the like.

Assuming that all the humidification water exists in the oxidant channel in the form of vapor, the volume flow rate $V_{in}$ (m$^3$/sec) of the humidified inlet air can be calculated using the following formula:

$$V_{in} = (n_{air} + W)RT_{in}/P_{in} \quad (9)$$

where $n_{air}$ (mol/sec) is the mass flow rate of the inlet air and R is a gas constant.

At steps 503–505, the pressure, temperature and mass flow rate in or of the inlet air are measured by the pressure sensor P, the temperature sensor T and the mass flow sensor F, respectively. The control section stores a map which represents the relation between these measured quantities and the oxygen concentration or nitrogen concentration in the inlet air beforehand. The oxygen concentration and nitrogen concentration in the inlet air are calculated using the stored map at steps 506 and 507, respectively. However, the oxygen concentration in the inlet air may be directly measured by an oxygen concentration sensor.

Next the volume flow rate of the inlet air is calculated at step 508 based on the pressure, temperature and mass flow rate in or of the inlet air. The mass flow rate $M_{out}$ (mol/sec) of the outlet air is calculated at step 509 using the following formula:

$$M_{out}=(n_{air}-I/4F)+W+I/2F \quad (10)$$

where $n_{air}$ (mol/sec) is the mass flow rate of the inlet air, I (A) is the output current of the fuel cell 1, F is Faraday constant, and W (mol/sec) is the mass rate of the humidification water. In formula (10), term "I/4F" represents the mass rate of oxygen consumed during the reaction and term "I/2F" represents the mass rate of water generated during the reaction.

The pressure and temperature in the outlet air is measured by the pressure sensor R and the temperature sensor T at steps 510 and 511, respectively. Then, assuming that all the water generated when electric power is produced exists in the form of vapor in the oxidant channel, the volume flow rate $V_{out}$ (m³/sec) of the outlet air is calculated at step 512 using the following formula:

$$V_{out}=M_{out}RT_{cell}/P_{out} \quad (11)$$

where R is a gas constant, $T_{cell}$ is the temperature of the fuel cell 1 and $P_{out}$ (Pa) is the pressure in the outlet air.

The humidity $C_{out}$ (mol/m³) in the outlet air is expressed as:

$$C_{out}=(C_{in}V_{in}/V_{out})+I/2FV_{out} \quad (12)$$

where $C_{in}$ (mol/m³) is the humidity in the inlet air, $V_{in}$ (m³/sec) is the volume flow rate of the inlet air and $V_{out}$ (m³/sec) is the volume flow rate of the outlet air. Thus the humidity $C_{out}$ in the outlet air is obtained using the humidity $C_{in}$ and the volume flow rate $V_{in}$ in or of the inlet air, the volume flow rate $V_{out}$ of the outlet air and the measured current I of the fuel cell 1. Accordingly the humidity in the outlet air is calculated at step 513 using formula (12).

Next the oxygen concentration in the outlet air is calculated at step 514 using the oxygen concentration and the volume flow rate in or of the inlet air, the volume flow rate of the outlet air and the measured current I of the fuel cell 1. The nitrogen concentration in the outlet air is calculated at step 515 using the volume flow rates of the inlet air and outlet air and the nitrogen concentration in the inlet air. Then, assuming that the humidity increases linearly between the inlet and outlet, the water distribution in the fuel cell 1 is estimated at step 516 based on the estimated humidity in the inlet air and outlet air.

At step 517, the temperature of the electrolyte membrane 10 is measured by the temperature sensor T. The saturated vapor concentration varies depending on the temperature of the electrolyte membrane 10. Therefore, based on the temperature measured at step 517, the amount of the condensed water in the fuel cell 1 is estimated as the FWC index at step 518. The FWC index thus calculated represents the amount of the condensed water after the inside of the fuel cell 1 reaches a steady state.

Figure 10:
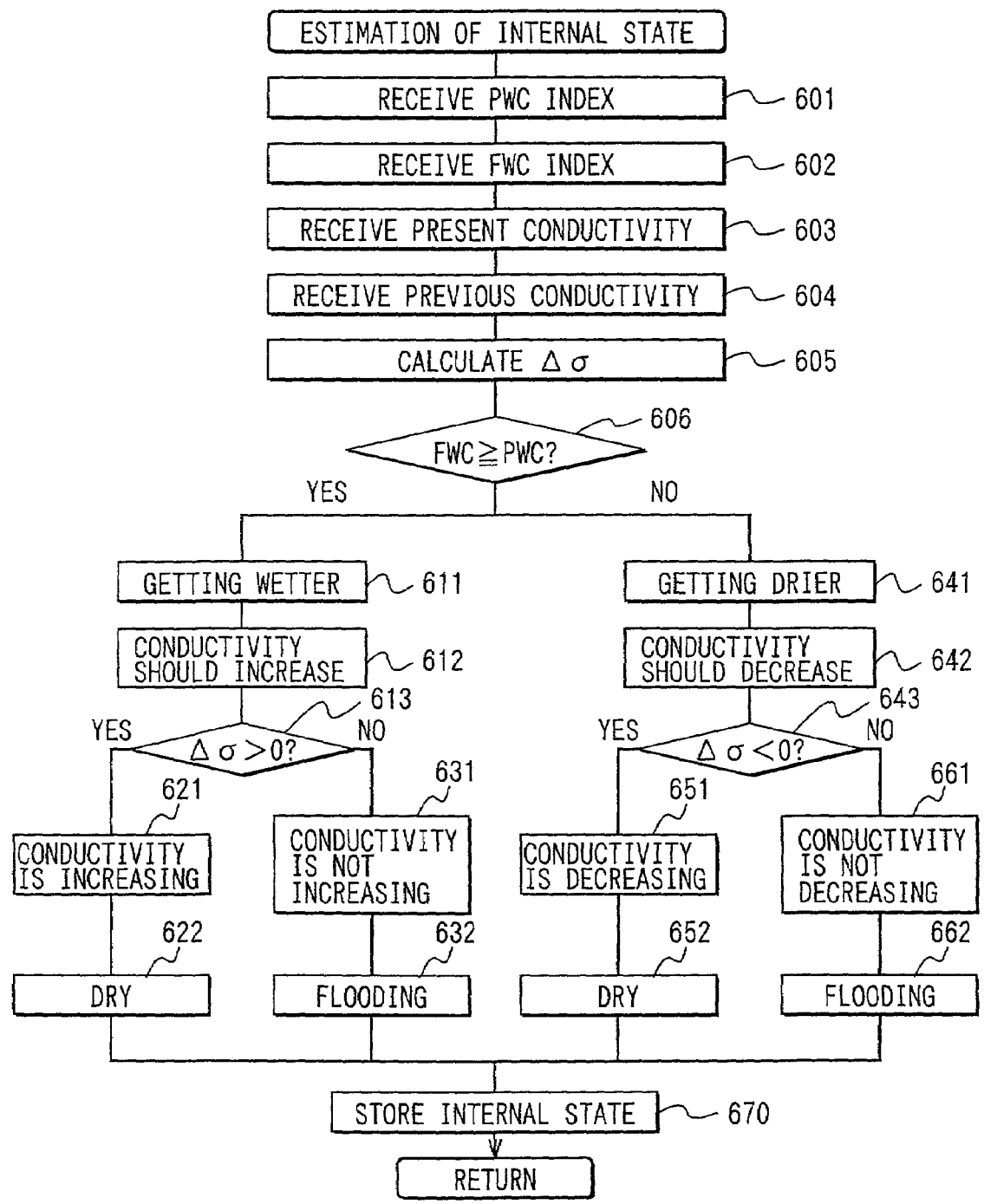
FIG. 10 is a flowchart of a subroutine which determines whether the water content is short or excessive based on the PWC index and FWC index at step 303 of FIG. 3.

Next, at step 303, it is determined whether the inside of the fuel cell 1 is dry or flooding as follows. Referring to FIG. 10, the values of the PWC index and the FWC index are received at steps 601 and 602, respectively. Further the present value and the previous value of the average conductivity $\sigma_{mesured}$ of the electrolyte membrane 10 are received at steps 603 and 604, respectively. Then the difference $\Delta\sigma$ between the present value and previous value of the conductivity $\sigma_{mesured}$ is calculated at step 605. It is determined at step 606 whether the FWC index is equal to or larger than the PWC index.

If yes, it is determined at step 611 that the inside of the fuel cell 1 is getting wetter. Then it is inferred at step 612 that the conductivity $\sigma_{mesured}$ of the electrolyte membrane 10 increases as the inside of the fuel cell 1 becomes wetter. It is determined at step 613 whether the difference $\Delta\sigma$ calculated at step 605 is larger than zero. If yes, it is determined at step 621 that the conductivity $\sigma_{mesured}$ is increasing due to increase in water content of the inside of the fuel cell 1. Therefore it is determined at 622 that the inside of the fuel cell 1 is dry. If it is determined at step 631 that the difference $\Delta\sigma$ is equal to or less than zero, it is determined at step 631 that the conductivity $\sigma_{mesured}$ is not increasing although the inside of the fuel cell 1 is getting wetter. Therefore it is determined at step 632 that the inside of the fuel cell 1 is flooding.

On the other hand, if it is determined at step 606 that the FWC index is less than the PWC index, it is determined at step 641 that the inside of the fuel cell 1 is getting drier. Then it is inferred at step 642 that the conductivity $\sigma_{mesured}$ of the electrolyte membrane 10 decreases as the inside of the fuel cell 1 becomes drier. It is determined at step 643 whether the difference $\Delta\sigma$ calculated at step 605 is less than zero. If yes, it is determined at step 651 that the conductivity $\sigma_{mesured}$ is decreasing due to decrease in water content of the inside of the fuel cell 1. Therefore it is determined at 652 that the inside of the fuel cell 1 is dry. If it is determined at step 643 that the difference $\Delta\sigma$ is equal to or larger than zero, it is determined at step 661 that the conductivity $\sigma_{mesured}$ is not decreasing although the inside of the fuel cell 1 is getting drier. Therefore it is determined at step 662 that the inside of the fuel cell 1 is flooding.

Finally, information on the internal state of the fuel cell 1 is stored at step 670. The control section controls the amount of the humidification water added to the inlet air and/or inlet hydrogen based on the stored information on the internal state of the fuel cell 1, so that the water content of the electroly temembrane 10 is kept proper. In this way, the resistance of the electrolyte membrane 10 is prevented from varying beyond an allowance, and consequently the output voltage of the fuel cell 1 is maintained without lowering.

According to the present embodiment, the PWC index and the FWC index are compared, and it is inferred based on the result of the comparison whether the conductivity of the electrolyte membrane 10 is increasing or decreasing. Further the present conductivity and the previous conductivity of the electrolyte membrane 10 are compared, and it is determined based on the result of comparison whether the conductivity of the electrolyte membrane 10 is actually increasing or decreasing. Then the internal state of the fuel cell 1 is estimated based on whether the inference agrees with the determination. Thus the internal state of the fuel cell 1 can be estimated readily but accurately discriminating between a drop in the output voltage due to short age of water content of the electrolyte membrane 10 and a drop in the output voltage due to excess of water content in the oxidant channel.

(Second Embodiment)

According to a second embodiment of the present invention, the closest-to-inlet point Xp at which the condensed water exists in the inside (i.e., the oxidant channel) of the fuel cell 1 is calculated, and used as an FWC index. Further the closest-to-inlet point Xp' at which the conductivity $\sigma_m$ of the electrolyte membrane 10 equals the saturation conductivity $\sigma_{max}$ is calculated, and used as a PWC index. Then the FWC index and PWC index are compared, and it is determined whether the water content of the inside of the fuel cell 1 is excessive or short based on the result of the comparison.

The closest-to-inlet point Xp at which condensed water exists is calculated as follows. The saturated vapor concentration, which is the maximum amount of water that can exists in the oxidant channel in the form of vapor, depends on the temperature $T_{cell}$ of the fuel cell 1. Accordingly, the saturated vapor concentration $C_s$(mol/m$^3$) is expressed as:

$$Cs=Ps(T_{cell})/RT_{cell} \quad (13)$$

where Ps (Pa) is the saturated vapor pressure.

Figure 11:
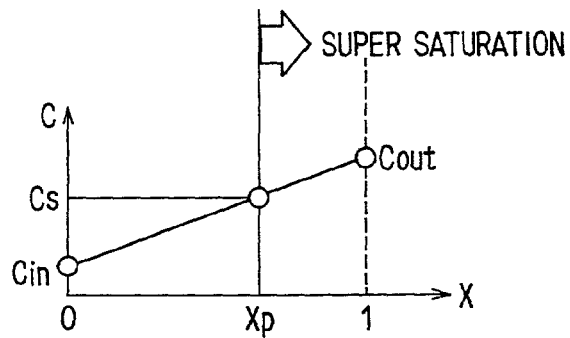
FIG. 11 is a graph showing the closest-to-inlet point Xp at which condensed water exists in the oxidant channel, which is used as an FWC index according to a second embodiment of the present invention.

The point Xp corresponds to a point at which the vapor concentration (i.e., the humidity) reaches a point of saturation. Assuming that the water content at a point in the oxidant channel increases linearly as the point comes close to the outlet as shown in FIG. 11, the point Xp can be obtained using the following formula:

$$Xp=CS-C_{in}/C_{out}-C_{in} \quad (14)$$

where $C_{in}$ is the humidity in the inlet air and $C_{out}$ is the humidity in the outlet air. Accordingly the point Xp is calculated using formula (14). The point Xp thus calculated represents the closest-to-inlet point at which condensed water exists after the inside of the fuel cell 1 reaches a steady state. Therefore the point Xp equals the point Xp' after the inside of the fuel cell 1 reaches a steady state.

Figure 12:
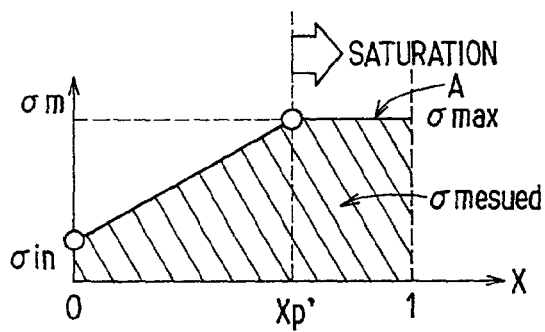
FIG. 12 is a graph showing the closest-to-inlet point Xp' at which the conductivity of the electrolyte equals the saturation conductivity, which is used as a PWC index according to the second embodiment.

The closest-to-inlet point Xp' at which the conductivity $\sigma_m$ of the electrolyte membrane 10 equals the saturation conductivity $\sigma_{max}$ is calculated as follows. Generally, the conductivity of the electrolyte membrane 10 distributes in the oxidant channel as shown by line A in FIG. 12, and the area of a polygon defined by the horizontal and vertical axes and line A equals the average conductivity. The measured conductivity $\sigma_{mesured}$ represents the average conductivity as described above. Accordingly the closest-to-inlet point Xp' at which the conductivity $\sigma_m$ equals the saturation conductivity $\sigma_{max}$ is expressed as:

$$Xp'=2(\sigma_{max}-\sigma_{mesured})/(\sigma_{max}-\sigma_{in}) \quad (15)$$

where $\sigma_{max}$ is the saturation conductivity and $\sigma_{in}$ is the conductivity on the inlet side. The saturation conductivity $\sigma_{max}$ is the conductivity at the point where the condensed water exists, and therefore known. The conductivity on the inlet side can be obtained using formula (3). Therefore the point Xp' can be obtained using formula (15). In this way, the point Xp' (PWC index) and the point Xp (FWC index) can be obtained using the measured physical quantities.

Figure 13:
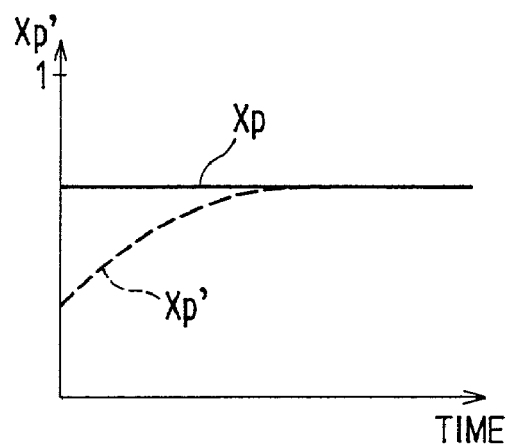
FIG. 13 is a graph showing that the point Xp' closer to the inlet than the point Xp comes close to the outlet over time so as to approach the point Xp, when the water content of the fuel cell is slightly excessive but approaches a proper value.
Figure 14:
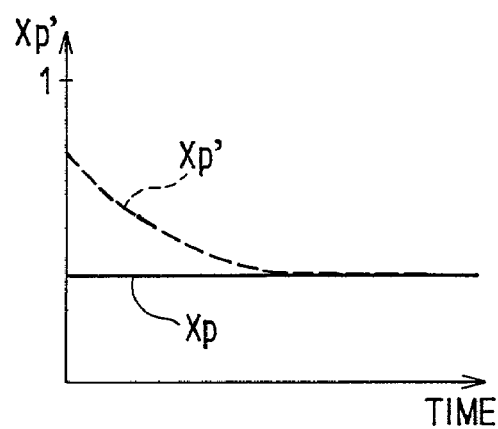
FIG. 14 is a graph showing that the point Xp' closer to the outlet than the point Xp comes close to the inlet over time so as to approach the point Xp, when the water content of the fuel cell is short but increasing.
Figure 15:
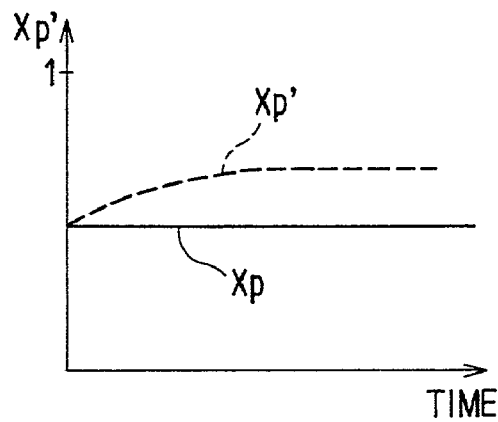
FIG. 15 is a graph showing the point Xp' gets away from the point Xp over time due to the excess of water content of the oxidant channel.

Then it is determined whether the water content of the inside of the fuel cell 1 is excessive or short as follows. When the water content is not excessive, the point (PWC index) Xp' approaches the point (FWC index) Xp over time as shown in FIGS. 13 and 14 if the operating condition of the fuel cell 1 is maintained. Therefore, if the difference between the points Xp' and Xp is equal to or less than a predetermined value and the points Xp' approaches the point Xp over time, it is determined that the water content at this time is proper.

If the difference is larger than the predetermined value and the points Xp' approaches the point Xp over time, it is determined that the water content at this time is not proper but approaches a proper value. When the point Xp' is less than the point Xp and comes close to the outlet over time so as to approach the point Xp as shown in FIG. 13, it is determined that the water content is slightly excessive at this time but approaches a proper value. When the point Xp' is larger than the point Xp and comes close to the inlet over time so as to approach the point Xp as shown in FIG. 14, it is determined that the water content is short at this time but increasing.

On the other hand, if the difference between the points Xp' and Xp increases over time as shown in FIG. 14, it is determined that the water content of the oxidant channel is excessive. In this case, the measured conductivity $\sigma_{mesured}$ apparently decreases over time although the actual conductivity does not decrease, because the excessive water obstructs the reaction in the fuel cell 1. Therefore the point Xp' gets away from the point Xp over time.

(Modifications)

In the first embodiment, the humidity in the inlet air is directly detected by the humidity sensor H at step 411 of FIG. 4. However, the humidity in the inlet air is not required to be directly measured.

In the second embodiment, the closest-to-inlet point Xp (i.e., FWC index) at which condensed water exists is calculated using the humidity $C_{in}$, $C_{out}$ in the inlet and outlet of the oxidant channel and the volume flow rates $V_{in}$, $V_{out}$ of the inlet air and outlet air. However, the point Xp may be calculated using the humidity in the inlet and outlet of the fuel channel and the volume flow rate of the inlet hydrogen and outlet hydrogen instead.

The present invention is not limited to the above embodiment and modifications, but may be variously embodied within the scope of the invention.

What is claimed is:

1. A method for determining whether water content of an inside of a fuel cell is short of excessive, said method comprising the steps of:

measuring water content of the inside of said fuel cell as an index of present water content (PWC) based on conductivity of electrolyte of said fuel cell;

estimating, as an index of future water content (FWC), water content of the inside of said fuel cell at a time point when time elapsed after said measuring step is performed reaches a predetermined length;

comparing said PWC index and said FWC index; and determining whether the water content of the inside of said fuel cell is short or excessive based on a result of said comparing step; wherein said measuring step comprises the steps of:

measuring an output voltage and an output current of said fuel cell;

estimating a voltage drop corresponding to resistance of the electrolyte of said fuel cell based on said measured output voltage of said fuel cell;

calculating said resistance of said electrolyte by dividing said voltage drop by said measured output current of said fuel cell;

calculating a reciprocal of said resistance of said electrolyte;

calculating, as measured conductivity, the conductivity of said electrolyte using said reciprocal of said resistance;

obtaining inlet-side conductivity of said electrolyte;

obtaining saturation conductivity of said electrolyte; and calculating, as said PWC index, a point Xp' at which conductivity equals said saturation conductivity based on said measured conductivity, said inlet-side conductivity and said saturation conductivity; and at said step of calculating said point Xp', said point Xp' is calculated using the following formula:

$$Xp'=2(\sigma_{max}-\sigma_{mesured})/(\sigma_{max}-\sigma_{in})$$

where $\sigma_{max}$ is said saturation conductivity, $\sigma_{mesured}$ is said measured conductivity, and $\sigma_{in}$ is said inlet-side conductivity.

2. A method for determining whether water content of an inside of a fuel cell is short of excessive, said method comprising the steps of:

measuring water content of the inside of said fuel cell as an index of present water content (PWC) based on conductivity of electrolyte of said fuel cell;

estimating, as an index of future water content (FWC), water content of the inside of said fuel cell at a time point when time elapsed after said measuring step is performed reaches a predetermined length;

comparing said PWC index and said FWC index; and determining whether the water content of the inside of said fuel cell is short or excessive based on a result of said comparing step; wherein said estimating step comprises the steps of:

obtaining saturated vapor concentration in an oxidant channel of said fuel cell;

obtaining humidity in an inlet of said oxidant channel;

obtaining humidity in an outlet of said oxidant channel; and calculating, as said FWC index, a point Xp at which condensed water exists in said oxidant channel based on said saturated vapor concentration, said water humidity in said inlet and said humidity in said outlet.

3. A method as in claim 2, wherein, at said step of calculating said point Xp, said point Xp is calculated using the following formula:

$$Xp=Cs-C_{in}/C_{out}=C_{in}$$

where Cs is said saturated vapor concentration, $C_{in}$ is said humidity in said inlet and $C_{out}$ is said humidity in said outlet.

4. A method for determining whether water content of an inside of a fuel cell is short of excessive, said method comprising the steps of:

measuring water content of the inside of said fuel cell as an index of present water content (PWC) based on conductivity of electrolyte of said fuel cell;

estimating, as an index of future water content (FWC), water content of the inside of said fuel cell at a time point when time elapsed after said measuring step is performed reaches a predetermined length;

comparing said PWC index and said FWC index; and determining whether the water content of the inside of said fuel cell is short or excessive based on a result of said comparing step; wherein said measuring step comprises the steps of:

measuring an output voltage and an output current of said fuel cell;

estimating a voltage drop corresponding to resistance of the electrolyte of said fuel cell based on said measured output voltage of said fuel cell;

calculating said resistance of said electrolyte by dividing said voltage drop by said measured output current of said fuel cell;

calculating a reciprocal of said resistance of said electrolyte;

calculating, as measured conductivity, the conductivity of said electrolyte using said reciprocal of said resistance;

obtaining inlet-side conductivity of said electrolyte;

obtaining saturation conductivity of said electrolyte; and calculating, as said PWC index, a point Xp' at which conductivity equals said saturation conductivity based on said measured conductivity, said inlet-side conductivity and said saturation conductivity; and said step of estimating said FWC index comprises the steps of:

obtaining saturated vapor concentration in an oxidant channel of said fuel cell;

obtaining humidity in an inlet of said oxidant channel;

obtaining humidity in an outlet of said oxidant channel; and calculating, as said FWC index, a point Xp at which the condensed water exists in said oxidant channel based on said saturated vapor concentration, said humidity in said inlet and said humidity in said outlet;

difference between said point Xp' and said point Xp is calculated at said comparing step; and said determining step comprises the steps of:

determining that the water content of the inside of said fuel cell is proper if said difference between said point Xp' and said point Xp is equal to or less than a predetermined value and thereafter said point Xp' approaches said point Xp over time; and determining that the water content of the inside of said fuel cell is excessive if said difference between said point Xp' and said point Xp increases over time.

5. A method for determining whether water content of an inside of a fuel cell is short of excessive, said method comprising the steps of:

measuring water content of the inside of said fuel cell as an index of present water content (PWC) based on conductivity of electrolyte of said fuel cell;

estimating, as an index of future water content (FWC), water content of the inside of said fuel cell at a time point when time elapsed after said measuring step is performed reaches a predetermined length;

comparing said PWC index and said FWC index;

determining whether the water content of the inside of said fuel cell is short or excessive based on a result of said comparing step;

controlling at least one of amount of humidification water added to air and hydrogen injected into electrolyte, flow rates of said air and said hydrogen, pressure in said air and said hydrogen and temperature of said air and said hydrogen based on a result of said determining step.

6. A method for determining whether water content of an inside of a fuel cell is short of excessive, said method comprising the steps of:

estimating present condensed water content of the inside of said fuel cell as an index of present water content (PWC) based on the conductivity of electrolyte of said fuel cell;

estimating, as an index of future water content (FWC), future condensed water content of the inside of said fuel cell at a time point when time elapsed after said estimating present condensed water content step is performed reaches a predetermined length;

comparing said PWC index and said FWC index; and determining whether the water content of the inside of said fuel cell is short or excessive based on a result of said comparing step; wherein said estimating present condensed water step comprises the steps of:
measuring an output voltage and an output current of said fuel cell;
estimating a voltage drop corresponding to resistance of electrolyte of said fuel cell based on said measured output voltage of said fuel cell;
calculating said resistance of said electrolyte by dividing said voltage drop by said measured output current of said fuel cell;
calculating a reciprocal of said resistance of said electrolyte;
calculating, as measured conductivity, conductivity of said electrolyte using said reciprocal of said resistance;
obtaining inlet-side conductivity of said electrolyte;
obtaining saturation conductivity of said electrolyte; and
calculating, as said PWC index, a point Xp' at which conductivity equals said saturation conductivity based on said measured conductivity, said inlet-side conductivity and said saturation conductivity; and
at said step of calculating said point Xp', said point Xp' is calculated using the following formula:

$$Xp'=2(\sigma_{max}-\sigma_{mesured})/(\sigma_{max}-\sigma_{in})$$

where $\sigma_{max}$ is said saturation conductivity, $\sigma_{mesured}$ is said measured conductivity, and $\sigma_{in}$ is said inlet-side conductivity.

7. A method for determining whether water content of an inside of a fuel cell is short of excessive, said method comprising the steps of:
estimating present condensed water content of the inside of said fuel cell as an index of present water content (PWC) based on the conductivity of electrolyte of said fuel cell;
estimating, as an index of future water content (EWC), future condensed water content of the inside of said fuel cell at a time point when time elapsed after said estimating present condensed water content step is performed reaches a predetermined length;
comparing said PWC index and said FWC index; and
determining whether the water content of the inside of said fuel cell is short or excessive based on a result of said comparing step; wherein
said estimating future condensed water content step comprises the steps of:
obtaining saturated vapor concentration in an oxidant channel of said fuel cell;
obtaining humidity in an inlet of said oxidant channel;
obtaining humidity in an outlet of said oxidant channel; and
calculating, as said FWC index, a point Xp at which condensed water exists in said oxidant channel based on said saturated vapor concentration, said water humidity in said inlet and said humidity in said outlet.

8. A method as in claim 7, wherein, at said step of calculating said point Xp, said point Xp is calculated using the following formula:

$$Xp=Cs-C_{in}/C_{out}-C_{in}$$

where Cs is said saturated vapor concentration, $C_{in}$ is said humidity in said inlet and $C_{out}$ is said humidity in said outlet.

9. A method for determining whether water content of an inside of a fuel cell is short of excessive, said method comprising the steps of:
estimating present condensed water content of the inside of said fuel cell as an index of present water content (PWC) based on the conductivity of electrolyte of said fuel cell;
estimating, as an index of future water content (FWC), future condensed water content of the inside of said fuel cell at a time point when time elapsed after said estimating present condensed water content step is performed reaches a predetermined length;
comparing said PWC index and said FWC index; and
determining whether the water content of the inside of said fuel cell is short or excessive based on a result of said comparing step; wherein
said estimating present condensed water step comprises the steps of:
measuring an output voltage and an output current of said fuel cell;
estimating a voltage drop corresponding to resistance of electrolyte of said fuel cell based on said measured output voltage of said fuel cell;
calculating said resistance of said electrolyte by dividing said voltage drop by said measured output current of said fuel cell;
calculating a reciprocal of said resistance of said electrolyte;
calculating, as measured conductivity, conductivity of said electrolyte using said reciprocal of said resistance;
obtaining inlet-side conductivity of said electrolyte;
obtaining saturation conductivity of said electrolyte; and
calculating, as said PWC index, a point Xp' at which conductivity equals said saturation conductivity based on said measured conductivity, said inlet-side conductivity and said saturation conductivity; and
said step of estimating said FWC index comprises the steps of:
obtaining saturated vapor concentration in an oxidant channel of said fuel cell;
obtaining humidity in an inlet of said oxidant channel;
obtaining humidity in an outlet of said oxidant channel; and
calculating, as said FWC index, a point Xp at which the condensed water exists in said oxidant channel based on said saturated vapor concentration, said humidity in said inlet and said humidity in said outlet;
difference between said point Xp' and said point Xp is calculated at said comparing step; and
said determining step comprises the steps of:
determining that the water content of the inside of said fuel cell is proper if said difference between said point Xp' and said point Xp is equal to or less than a predetermined value and thereafter said point Xp' approaches said point Xp over time; and
determining that the water content of the inside of said fuel cell is excessive if said difference between said point Xp' and said point Xp increases over time.

10. A method for determining whether water content of an inside of a fuel cell is short of excessive, said method comprising the steps of:
estimating present condensed water content of the inside of said fuel cell as an index of present water content (PWC) based on the conductivity of electrolyte of said fuel cell;
estimating, as an index of future water content (FWC), future condensed water content of the inside of said fuel cell at a time point when time elapsed after said estimating present condensed water content step is performed reaches a predetermined length;

comparing said PWC index and said FWC index;
determining whether the water content of the inside of said fuel cell is short or excessive based on a result of said comparing step;
controlling at least one of amount of humidification water added to air and hydrogen injected into electrolyte, flow rates of said air and said hydrogen, pressure in said air and said hydrogen and temperature of said air and said hydrogen based on a result of said determining step.

* * * * *